US00PP08624P

United States Patent [19]

Desclaux

[11] Patent Number: Plant 8,624

[45] Date of Patent: Mar. 1, 1994

[54] STANDARD CARNATION NAMED RIMINI

[75] Inventor: Jean-Louis Desclaux, Angers, France

[73] Assignee: Laboratorie De Physilogie Vegetale, Le Pradet, France

[21] Appl. No.: 971,407

[22] Filed: Nov. 4, 1992

[51] Int. Cl.[5] ..... A01H 5/00

[52] U.S. Cl. ..... Plt./73.1

[58] Field of Search ..... Plt. 73.1

*Primary Examiner*—Howard J. Locker

*Assistant Examiner*—Elizabeth C. Kemmerer

*Attorney, Agent, or Firm*—Tilton, Fallon, Lungmus & Chestnut

[57] ABSTRACT

A new and distinctive standard carnation cultivar particularly distinguished by its very large size flowers having an irregularly serrated edge. The petals are red with a greenish base. The flowers are carried on erect, thick stems, with a broad bell-shaped calyx.

1 Drawing Sheet

BACKGROUND OF THE NEW PLANT

This standard carnation cultivar originated as a hybrid seedling produced at San Remo, Italy by my crossing of two plants, hereinafter identified, selected from a field of various carnation varieties maintained at the nursery for breeding purposes. This particular seedling was selected from those produced by the said crossing because of the very unusual flower coloration on a plant having abundant foliage, favorable growth characteristics and resistance to *Fusarium oxysporum*. After isolation of the selected plant, vegetative propagation was made by cuttings or by in vitro culture. The said propagation was made at our laboratory located in Le Pradet, France. The new variety most resembles Lontarion (U.S. Plant Pat. No. 5,435). Rimini differs from Lontarion in a less fine and less regular serration of petals, a larger flower, a larger and wider calyx and a thicker stem. Under my direction, propagation was done by means of cuttings. The initial success of the propagation was continued through several successive generations which proved that the new variety retained all of the distinguished characteristics hold true from generation to generation and appear to be firmly fixed.

DESCRIPTION OF THE DRAWINGS

My new carnation cultivar is illustrated by the accompanying photographic drawing which, in full color, shows the form and coloration of the flowers as they appear. The colors shown are as nearly true to these herein specified as is reasonable possible to obtain by conventional photographic procedures.

DESCRIPTION OF THE NEW PLANT

The following is a detailed description of my new carnation plant as observed from plants grown under greenhouse conditions in Le Pradet, France with the stated flower colors being according to The R.H.S. Colour Chart of The Royal Horticultural Society of London, England.

THE PLANT

Origin: Seedling.

Parentage:

*Seed parent.*—Plant number 612.

*Pollen parent.*—Plant number 309.

These parent plants are so identified in my business records of the present cultivar maintained at the office of the San Remo nursery and the production of the aforementioned hybrid and the selected seedling are also there recorded. These parent plants have never been commercialized. Plant parent 612 is a red colored standard carnation with a diameter of 8 cm, serrated petals, and a stem length of about 60 centimeters. Plant parent 309 is also a standard carnation. Plant parent 309 is red in color, although the red is not very uniform, has a diameter of about 8 cm., with a large and very serrated petal and a stem length of about 60 cm.

Classification:

*Botanic.*—*Dianthus caryopyllus L.*

*Commercial.*—Standard carnation.

Form: An erect bush having at least 4 stems emitted near the ground, having vigorous upright growth habit.

Height: About 115 cm. at eight months.

Cane length: Less than 15 cm owing to pinching.

Branching character: The plant averages 4 to 5 main branches. These branches are prolonged by a vertical inflorescence which has, in the lower part, shoots which will produce flowers.

Strength: Rigid.

Foliage:

*Quantity.*—Abundant.

*Number of Leaves.*—More than 120.

*Size and shape of leaf.*—The leaf is at the 7th node, has a size of 18.4×1.1 cm., and is spindle shaped.

*Margin type.*—Recurved.

*Texture.*—Leathery.

*Color.*—Upper side R.H.S. 137A. Under side R.H.S. 137A.

*Ribs and veins.*—Hardly noticeable.

*Rachis.*—Hardly noticeable.

THE BUD

Size:

*Shape.*—Ovoid.

*Diameter.*—2.4 cm.

*Length.*—3 cm.

*Color of petals.*—When sepals first divide — same as full bloom which is R.H.S. 44B. When petals begin to unfurl, same as full bloom which is R.H.S. 44B.

Rate of opening: Normal.

Sepals:

*Shape.*—Joined at lower part and sharp-pointed at extremity.
*Number.*—5-7.
*Color.*—Inside: Pea green with traces of scarlet. R.H.S. 149D with traces of 43C. Outside: Scheele's green R.H.S. 143B.
*Striae.*—Longitudinal striae.

Calyx:
*Shape.*—Bell-shaped.
*Size.*—Broad.
*Aspect.*—Smooth.
*Splitting.*—Rarely.

Peduncle:
*Length.*—About 82 cm.
*Character.*—Erect rigid.
*Color.*—137A.
*Strength.*—Good.

THE FLOWER

Blooming habit: Recurrent and profuse.
Size of bloom: Very large.
*Diameter.*—About 9.7 cm.
*Depth.*—About 6.2 cm.
Borne: Singly.
Shape:
*When bloom first opens.*—High center.
*When bloom matures.*—Dome.

Petalage:
*Number of petals.*—80 (average).
*Form.*—Fan shaped with very serrated apex.
*Texture.*—Leathery.
*Appearance.*—Satiny.
*Color.*—Outer petals — red body 44B with greenish base, reverse side — red 44B. Inside petals — red body 44B with greenish base, reverse side — red 44B.

Petaloids: Number less than 10.
Discoloration after full bloom: No.
Persistence: Yes.
Lasting quality:
*As cut flower.*—At least 10 days.
Disease resistance: Tolerant to *Fusarium oxysporum.*
Fragrance: Perceptible.

REPRODUCTIVE ORGANS

Stamens:
*Number.*—8 to 13.
*Arrangement.*—Around the ovary.

Anthers:
*Size.*—Less than 0-4 cm.
*Color.*—Reddish.

Filaments:
*Length.*—About 1 cm.
*Color.*—Reddish.

Pistils:
*Number.*—3 to 4.

Styles:
*Length.*—2.1 cm.
*Color.*—Reddish.

Stigmas: Reddish.
Character of ovaries: Ribbed.
Pollen: Yes.
*Color.*—White.

I claim:

1. A new and distinctive hybrid standard carnation plant, substantially as herein shown and described, characterized in particular by its recurrent profuse production of very large size flowers, the petals of which are in general of reddish color, said plant having more than 120 leaves on a thick stems, with a bell-shaped thick calyx.

* * * * *

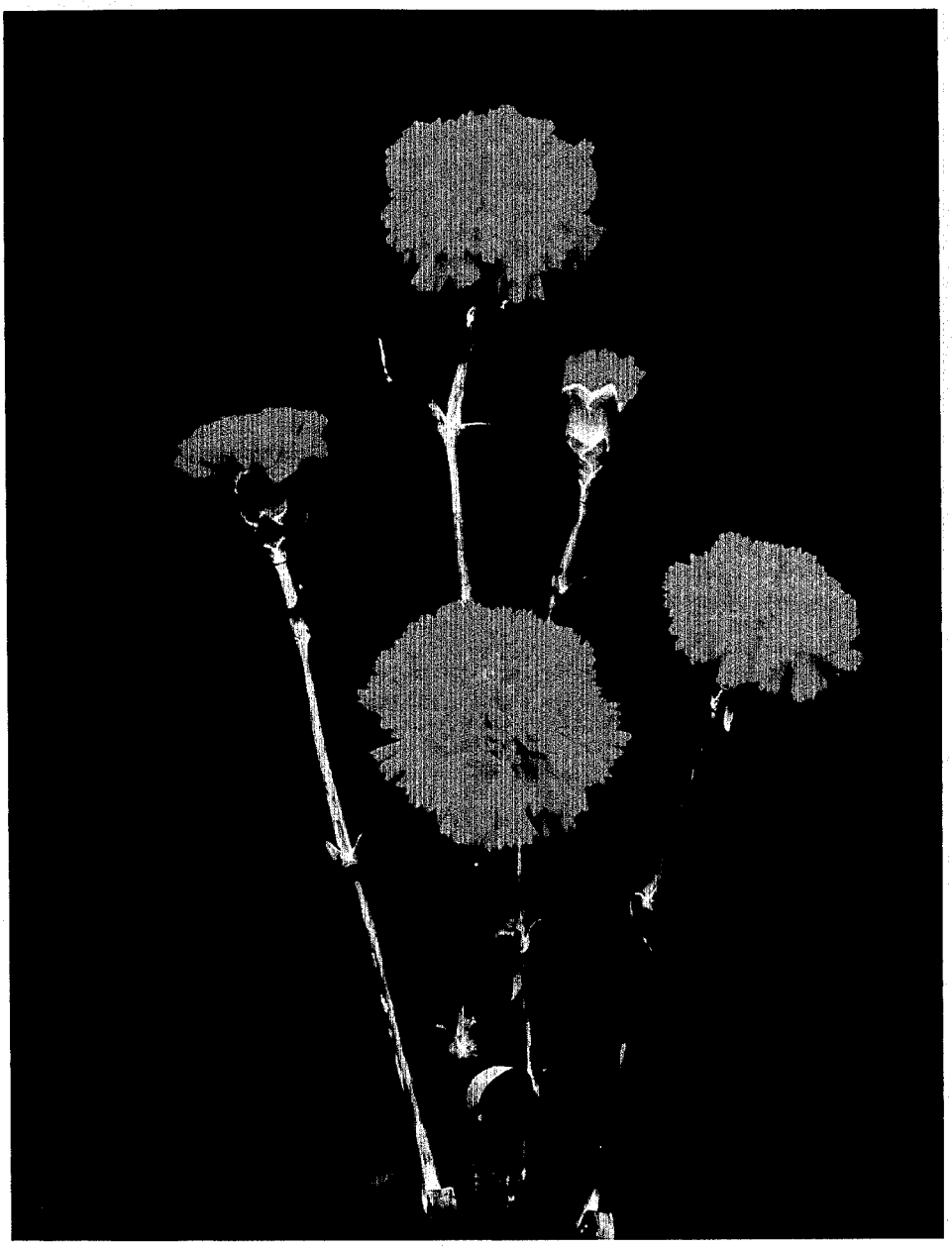

UNITED STATES PATENT AND TRADEMARK OFFICE

CERTIFICATE OF CORRECTION

PATENT NO. : Plant 8,624

DATED : March 1, 1994

INVENTOR(S) : Jean-Louis Desclaux

It is certified that error appears in the above-indentified patent and that said Letters Patent is hereby corrected as shown below:

Column 2, line 41, delete "2.4" and insert -- 2.3 --.

Signed and Sealed this

Eleventh Day of October, 1994

*Attest:*

*Attesting Officer*

Bruce Lehman

BRUCE LEHMAN

*Commissioner of Patents and Trademarks*